United States Patent
Huang et al.

(10) Patent No.: US 12,339,259 B1
(45) Date of Patent: Jun. 24, 2025

(54) MONITORING METHOD AND DEVICE OF DISSOLVED GREENHOUSE GASES IN WASTEWATER

(71) Applicants: Tongji University, Shanghai (CN); Fuzhou Water Group Co., Ltd., Fuzhou (CN)

(72) Inventors: Xiangfeng Huang, Shanghai (CN); Chen Cai, Shanghai (CN); Zhongqing Wei, Fuzhou (CN); Jia Liu, Shanghai (CN); Kaiming Peng, Shanghai (CN); Zhenxin Shang, Nanjing (CN)

(73) Assignees: Tongji University, Shanghai (CN); Fuzhou Water Group Co., Ltd., Fuzhou (CN)

( * ) Notice: Subject to any disclaimer, the term of this patent is extended or adjusted under 35 U.S.C. 154(b) by 0 days.

(21) Appl. No.: 18/973,214

(22) Filed: Dec. 9, 2024

(30) Foreign Application Priority Data

May 14, 2024 (CN) .......................... 202410592278.6

(51) Int. Cl.
*G01N 30/06* (2006.01)
*G01N 30/84* (2006.01)
(Continued)

(52) U.S. Cl.
CPC ............. *G01N 30/06* (2013.01); *G01N 30/84* (2013.01); *G01N 2030/025* (2013.01);
(Continued)

(58) Field of Classification Search
None
See application file for complete search history.

(56) References Cited

U.S. PATENT DOCUMENTS 3,545,929 A * 12/1970 Swinnerton .............. G01N 1/34
422/89

FOREIGN PATENT DOCUMENTS

CN 203148903 U * 8/2013
CN 105954415 A * 9/2016 ............. G01N 30/06
(Continued)

OTHER PUBLICATIONS

Fujian Strait Environmental Protection Group Co., Ltd. and Fuzhou Water Group Co., Ltd. (Applicants), Replacement claims (allowed) of CN202410592278.6, Oct. 23, 2024.
(Continued)

*Primary Examiner* — Daniel S Larkin
(74) *Attorney, Agent, or Firm* — Hemisphere Law, PLLC; Zhigang Ma

(57) ABSTRACT

A monitoring method of dissolved greenhouse gases in wastewater includes: S1, collecting a wastewater sample, performing mud-water separation, and collecting a supernatant after the mud-water separation; S2, adding dilute sulfuric acid solution to the supernatant collected in a headspace vial to adjust pH of the supernatant to 1-4, and then tightening a cap of the headspace vial; S3, inverting the headspace vial, and checking whether there are air bubbles in the headspace vial; S4, injecting 5-10 mL of pure nitrogen into the headspace vial through a syringe, and discharging 5-10 mL of the wastewater sample through a conduit; S5, placing the headspace vial in a water bath constant temperature shaker, and shaking the headspace vial for 20-30 minutes; S6, extracting gases from an upper part of the headspace vial, and measuring concentrations of the gases; S7, quantitatively calculating concentrations of the dissolved greenhouse gases in the wastewater sample.

7 Claims, 1 Drawing Sheet

(51) Int. Cl.
    *G01N 30/02* (2006.01)
    *G01N 33/18* (2006.01)
(52) U.S. Cl.
    CPC .................. *G01N 2030/065* (2013.01); *G01N 2030/8441* (2013.01); *G01N 33/188* (2013.01)

(56) References Cited

FOREIGN PATENT DOCUMENTS

| | | | | | |
|---|---|---|---|---|---|
| CN | 106018590 | B | * | 1/2018 | ............. G01N 30/02 |
| CN | 107192786 | B | * | 5/2018 | ............. G01N 30/02 |
| CN | 108020608 | A | * | 5/2018 | ............. G01N 30/06 |
| CN | 113866373 | A | * | 12/2021 | ......... G01N 33/1826 |
| CN | 114252539 | A | * | 3/2022 | ............. G01N 30/06 |
| CN | 114993774 | A | * | 9/2022 | |
| CN | 115096659 | A | * | 9/2022 | ........... G01N 1/2294 |
| CN | 116539682 | A | * | 8/2023 | ............. G01N 27/26 |
| CN | 116593235 | A | * | 8/2023 | ............... G01N 1/22 |
| DE | 1773510 | A | * | 11/1971 | ............. G01N 30/06 |
| DE | 19807839 | A | * | 9/1999 | ......... G01N 33/0047 |
| JP | 11142385 | A | * | 5/1999 | |
| JP | 2016166848 | A | * | 9/2016 | |
| KR | 20150044173 | A | * | 4/2015 | ............. G01N 30/02 |

OTHER PUBLICATIONS

CNIPA, Notification to grant patent right for invention in CN202410592278.6, Oct. 28, 2024.

\* cited by examiner

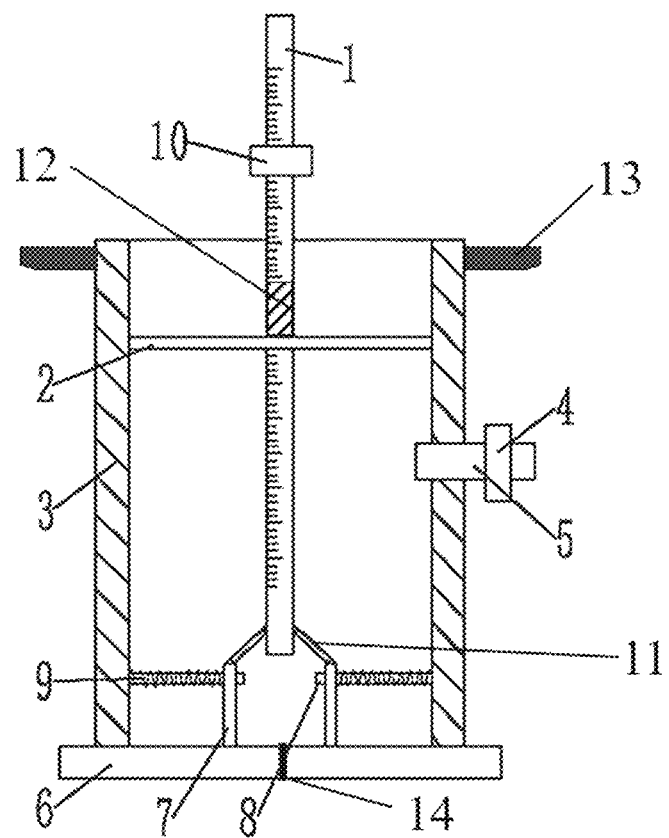

MONITORING METHOD AND DEVICE OF DISSOLVED GREENHOUSE GASES IN WASTEWATER

CROSS-REFERENCE TO RELATED APPLICATION

This application claims priority to Chinese Patent Application No. CN202410592278.6, filed May 14, 2024, which is herein incorporated by reference in its entirety.

TECHNICAL FIELD

The disclosure relates to the field of greenhouse gas monitoring technologies, and more particularly to a monitoring method and a device of dissolved greenhouse gases in wastewater.

BACKGROUND

Extreme climate changes such as global warming, rainfall and high temperature caused by excessive emissions of greenhouse gases are threatening the survival of human beings. Emissions of greenhouse gases from wastewater treatment plants have become a focus of environmental monitoring systems. The greenhouse gases including methane ($CH_4$) and nitrous oxide ($N_2O$) are intermediate products continuously produced and consumed during biochemical reactions of wastewater treatment, and they are affected by process operation parameters (such as dissolved oxygen abbreviated as DO, aeration intensity, sludge retention time abbreviated as SRT, etc.), changes of influent water quality conditions (such as influent ammonium ion abbreviated as $NH_4^+$, chemical oxygen demand abbreviated as COD, etc.) and environmental factors (such as temperature, extreme weather, etc.). Dissolved greenhouse gases are a transitional state from generation to release of the greenhouse gases and are also one of the indicators to determine whether the biochemical reactions in the wastewater treatment process are under optimal reaction conditions. Therefore, it is greatly significant to study emission reduction of the greenhouse gases in the wastewater treatment plants, and it is necessary to have a reasonable method for monitoring the dissolved greenhouse gases in wastewater.

SUMMARY

The disclosure provides a monitoring method and a device of dissolved greenhouse gases in wastewater to solve the existing problems in the related art.

In order to achieve the aforementioned purpose, the disclosure provides the monitoring method of the dissolved greenhouse gases in the wastewater, which includes the following steps:

S1, collecting a wastewater sample by using a wastewater collection device, performing mud-water separation on the wastewater sample, and collecting a supernatant after the mud-water separation by using a headspace vial;

S2, adding a dilute sulfuric acid solution to the supernatant collected in the headspace vial to adjust pH of the supernatant to 1-4, and then tightening a cap of the headspace vial;

S3, inverting the headspace vial, checking whether there are air bubbles in the headspace vial, discarding the wastewater sample and repeating the step S1 and the step S2 to recollect another wastewater sample when there are air bubbles in the headspace vial, and storing the headspace vial in a refrigerator when there are no air bubbles in the headspace vial;

S4, injecting 5-10 milliliters (mL) of pure nitrogen into the headspace vial by using a syringe, and discharging 5-10 mL of the wastewater sample from the headspace vial through a conduit;

S5, placing the headspace vial in a water bath constant temperature shaker, and shaking the headspace vial for 20-30 minutes to make a gas phase and a liquid phase in the headspace vial to reach headspace equilibrium;

S6, extracting gases from an upper part of the headspace vial in the step S5, and measuring concentrations of the gases by using a gas chromatograph; and S7, quantitatively calculating concentrations of the dissolved greenhouse gases in the wastewater sample of the step S1 based on Henry's Law and the concentrations of the gases as greenhouse gases in the gas phase measured in the step S6.

In an embodiment, a mass fraction of the dilute sulfuric acid solution in the step S2 is 20%.

In an embodiment, a storage temperature of the refrigerator in the step S3 is 0 degrees Celsius (° C.) to 4° C.

In an embodiment, the step S5 specifically includes: placing the headspace vial in the water bath constant temperature shaker and shaking the headspace vial under a condition of 25° C. and 150-200 revolutions (r) per minute for 20-30 minutes.

In an embodiment, the dissolved greenhouse gases include $N_2O$ and methane $CH_4$ in the step S7.

In an embodiment, a concentration calculation equation for the $N_2O$ is:

$$C_0 = \frac{(C_l \times V_l) + \left(\frac{C_g \times P}{R \times T} \times V_g\right)}{V_l + V_g}$$

$$C_l = C_g \times \exp\left(\left(A_1 + A_2 \times \left(\frac{100}{T}\right) + A_3 \times \ln\left(\frac{T}{100}\right) + A_4 \times \left(\frac{T}{100}\right)^2\right)\right)$$

where $C_0$ represents a concentration (micromoles per liter ($\mu mol \cdot L^{-1}$)) of the $N_2O$ in the wastewater sample, $C_g$ represents a concentration (parts per million (ppm), micromoles per mole ($\mu mol/mol$)) of the $N_2O$ in the gas phase after the headspace equilibrium, $C_l$ represents a concentration ($\mu mol \cdot L^{-1}$) of the $N_2O$ in the liquid phase after the headspace equilibrium, and P and R respectively represent an atmospheric pressure (101.325 kilopascal (kPa)) and a gas constant (8.314); T represents an absolute temperature (Kelvin (K)), $V_g$ and $V_l$ respectively represent volumes (mL) of the gas phase and liquid phase in the headspace vial, and $A_1$, $A_2$, $A_3$ and $A_4$ respectively represent constants −165.8806, 222.8743, 92.0792, and −1.48425;

In an embodiment, a concentration calculation equation for the $CH_4$ is:

$$C_0 = C_g\left(\frac{\beta RT}{V_m} + \frac{V_g}{V_l}\right)$$

where $C_0$ represents a concentration ($\mu mol \cdot L^{-1}$) of the $CH_4$ in the wastewater sample, $C_g$ represents a concentration ($\mu mol \cdot L^{-1}$) of the $CH_4$ in the gas phase after the headspace equilibrium, $\beta$ represents a solubility coefficient (0.03096 liters per liter per atmosphere ($L \cdot L^{-1} \cdot atm^{-1}$)) for the $CH_4$, R represents a gas state constant (0.08206 liters atmospheres per mole per Kelvin (L· atm·mol$^{-1}$·K$^{-1}$)), T represents the absolute temperature (K), $V_m$ represents a molar volume (22.356 liters per mole (L·mol$^{-1}$)) of the CH$_4$ under a standard condition, and $V_g$ and $V_l$ respectively represent the volumes (mL) of the gas phase and liquid phase in the headspace vial.

In an embodiment, a monitoring device for the dissolved greenhouse gases in the wastewater includes:

an open-top container, and two base plates are capable of horizontally sliding and are symmetrically disposed on a bottom of the open-top container; sliding seats are fixedly connected to top surfaces of the two base plates respectively, the sliding seats are disposed on ends of the two base plates close to each other, and the sliding seats are horizontally slide-connected to sliding rods respectively; ends of the sliding rods are fixedly connected to an inner wall of the open-top container respectively, springs are fixedly connected between the sliding seats and the inner wall of the open-top container respectively, and the springs are respectively sleeved to the sliding rods;

a rod, vertically disposed in the open-top container; a bottom of the rod is hinged to two hinge rods, the two hinge rods are respectively hinged to the sliding seats disposed on the top surfaces of the two base plates, the rod is slidably connected to a filter mesh with position limiting, the filter mesh is slidably matched to the inner wall of the open-top container, an outer wall of the rod is threaddedly connected to a threaded sleeve, and the threaded sleeve is rotatably connected to a top end of the filter mesh; and a connecting pipe horizontally and fixedly connected to a side wall of the open-top container, and a valve disposed on the connecting pipe.

In an embodiment, the rod is equipped with scale lines.

In an embodiment, a marker ring is sleeved to the rod.

The monitoring method and the device of the dissolved greenhouse gases in the wastewater provided by the disclosure discloses the following technical effect.

The monitoring method and the device of the dissolved greenhouse gases in the wastewater provided by the disclosure fills a gap in the monitoring method of the dissolved greenhouse gases, and through collection and quantification methods of the dissolved CH$_4$ and N$_2$O in a wastewater treatment system of the disclosure, it is possible to understand generation and release mechanisms of the greenhouse gases during a wastewater treatment process, thereby facilitating the control and treatment of the greenhouse gases produced in the wastewater treatment process.

BRIEF DESCRIPTION OF DRAWING

In order to provide a clearer explanation of embodiments of the disclosure or technical solutions in the related art, a brief introduction will be given below to the accompanying drawings required in the description of the embodiments or the related art. It is apparent that the accompanying drawings in the following description are some of the embodiments of the disclosure. For those skilled in the art, other drawings can be obtained based on structures shown in these drawings without creative labor.

FIGURE illustrates a schematic structural diagram of a monitoring device of dissolved greenhouse gases in wastewater according to the disclosure.

Description of reference numerals: 1, rod; 2, filter mesh; 3, open-top container; 4, valve; 5, connecting pipe; 6, base plate; 7, sliding seat; 8, sliding rod; 9, spring; 10, marker ring; 11, hinge rod; 12, threaded sleeve; 13, hand handle; 14, sealing element.

DETAILED DESCRIPTION OF EMBODIMENTS

The following will provide a clear and complete description of the technical solution in embodiments of the disclosure, in conjunction with the accompanying drawings. Apparently, the described embodiments are only a part of the embodiments of the disclosure, not all of them. Based on the embodiments in the disclosure, all other embodiments obtained by those skilled in the art without creative labor fall within the scope of protection of the disclosure.

In order to make the aforementioned objectives, features, and advantages of the disclosure more apparent and understandable, the following will provide a further detailed description of the disclosure in conjunction with the accompanying drawings and specific embodiments.

A monitoring method of dissolved greenhouse gases in wastewater provided by the disclosure includes the following steps.

S1, the wastewater sample is collected by using a wastewater collection device, mud-water separation is performed on the wastewater sample, and a supernatant is collected after the mud-water separation by using a headspace vial;

S2, the supernatant collected in the headspace vial is added with a dilute sulfuric acid solution to adjust pH of the supernatant to 1-4, and a cap of the headspace vial is tightened;

S3, the headspace vial is inverted, and whether there are air bubbles in the headspace vial is checked; if there are air bubbles in the headspace, the wastewater sample is discarded and the step S1 and the step S2 are repeated to recollect another wastewater sample, and if there are no air bubbles in the headspace, the headspace vial is stored in a refrigerator;

S4, 5-10 mL of pure nitrogen is injected into the headspace vial by using a syringe, and 5-10 mL of the wastewater sample is discharged from the headspace vial through a conduit, wherein a volume of the headspace vial is 20 mL, and 10 mL of the pure nitrogen is injected into the headspace vial by using a 10 ml syringe (equipped with a 1.2*30 needle);

S5, the headspace vial is placed in a water bath constant temperature shaker and is shaken for 20-30 minutes to make a gas phase and a liquid phase in the headspace vial to reach headspace equilibrium;

S6, gases from an upper part of the headspace vial in the step S5 is extracted, and concentrations of the gases are measured by using a gas chromatography; and S7, based on Henry's Law and the concentrations of the gases as greenhouse gases in the gas phase measured in the step S6, concentrations of the dissolved greenhouse gases in the wastewater sample of the step S1 are quantitatively calculated.

Preferably, in the step S2, a mass fraction of the dilute sulfuric acid solution is 20%.

Preferably, in the step S3, a storage temperature of the refrigerator is 0° C. to 4° C.

Preferably, in the step S5, the headspace vial is placed in the water bath constant temperature shaker and is shaken under a condition of 25° C. and 150-200 r per minute for 20-30 minutes.

Preferably, in the step S7, the dissolved greenhouse gases include N$_2$O and CH$_4$.

Preferably, a concentration calculation equation for the N₂O is:

$$C_0 = \frac{(C_l \times V_l) + \left(\frac{C_g \times P}{R \times T} \times V_g\right)}{V_l + V_g}$$

$$C_l = C_g \times \exp\left(\left(A_1 + A_2 \times \left(\frac{100}{T}\right) + A_3 \times \ln\left(\frac{T}{100}\right) + A_4 \times \left(\frac{T}{100}\right)^2\right)\right)$$

where $C_0$ represents a concentration (μmol·L⁻¹) of the N₂O in the wastewater sample, $C_g$ represents a concentration (ppm, μmol/mol) of the N₂O in the gas phase after the headspace equilibrium, $C_l$ represents a concentration (μmol·L⁻¹) of the N₂O in the liquid phase after the headspace equilibrium, and P and R respectively represent an atmospheric pressure (101.325 kPa) and a gas constant (8.314); T represents an absolute temperature (K), $V_g$ and $V_l$ respectively represent volumes (mL) of the gas phase and liquid phase in the headspace vial, and $A_1$, $A_2$, $A_3$ and $A_4$ respectively represent constants −165.8806, 222.8743, 92.0792, and −1.48425.

Preferably, a concentration calculation equation for the CH₄ is:

$$C_0 = C_g\left(\frac{\beta RT}{V_m} + \frac{V_g}{V_l}\right)$$

where $C_0$ represents a concentration (μmol·L⁻¹) of the CH₄ in the wastewater sample, $C_g$ represents a concentration (μmol·L⁻¹) of the CH₄ in the gas phase after the headspace equilibrium, β represents a solubility coefficient (0.03096 L·L⁻¹·atm⁻¹) for the CH₄, R represents a gas state constant (0.08206 L·atm·mol⁻¹·K⁻¹), T represents the absolute temperature (K), $V_m$ represents a molar volume (22.356 L·mol⁻¹) of the CH₄ under a standard condition, and $V_g$ and $V_l$ respectively represent the volumes (mL) of the gas phase and liquid phase in the headspace vial.

Referring to the FIGURE, the disclosure further discloses a monitoring device for the dissolved greenhouse gases in the wastewater, which includes:

an open-top container 3, and the two base plates 6 are capable of horizontally sliding and are symmetrically disposed on a bottom of the open-top container 3; sliding seats 7 are fixedly connected to top surfaces of the two base plates 6, the sliding seats 7 are disposed on ends of the two base plates 6 close to each other, and the sliding seats 7 are horizontally slide-connected to sliding rods 8 respectively; ends of the sliding rods 8 are fixedly connected to an inner wall of the open-top container 3 respectively, springs 9 are fixedly connected between the sliding seats 7 and the inner wall of the open-top container 3 respectively, and the springs 9 are respectively sleeved to the sliding rods 8. It should be considered that during an actual use, the two base plates 6 may appear to deviate during a sliding process, therefore, it is necessary to provide sliding grooves at a bottom of the open-top container 3 to limit a position of the two base plates 6, thereby ensuring stable sliding between the two base plates 6 and the open-top container 3.

A rod 1 is vertically disposed in the open-top container 3, a bottom of the rod 1 is hinged to two hinge rods 11, and the two hinge rods 11 are respectively hinged to the sliding seats 7 disposed on the top surfaces of the two base plates 6; the rod 1 is slidably connected to a filter mesh 2 with position limiting, and the filter mesh 2 is slidably matched to the inner wall of the open-top container 3; an outer wall of the rod 1 is threadedly connected to a threaded sleeve 12, and the threaded sleeve 12 is rotatably connected to a top end of the filter mesh 2.

A connecting pipe 5 is horizontally and fixedly connected to a side wall of the open-top container 3, and a valve 4 is disposed on the connecting pipe 5.

The open-top container 3 is provided with a hand handle 13. When the monitoring device is in use, the rod 1 is configured to lower the monitoring device into a wastewater treatment pool, which allows wastewater to fill the open-top container 3. The rod 1 defines a width, and a depth of a collected wastewater sample is preset through a marker ring 10 to make it easy to clearly judge a depth of collected wastewater (i.e., the collected wastewater sample). When the wastewater in the open-top container 3 reaches a preset water depth, the monitoring device is removed from the wastewater treatment pool, and the threaded sleeve 12 is rotated to move the filter mesh 2 to a position below a water outlet, achieving the mud-water separation rapidly. Afterwards, the valve 4 is opened, and the supernatant in the wastewater is collected from the water outlet by using the headspace vial, and the valve 4 is closed after the collection is completed. With one hand holding the hand handle and the other hand pushing the rod 1, the sliding seats 7 respectively slide relative to the sliding rods 8, which pushes the two base plates 6 at the bottom of the open-top container 3 to separate and makes muddy water at the bottom of the open-top container 3 be discharged from the monitoring device, facilitating subsequent continued collection. The filter mesh 2 can also be moved further down to near the bottom of the open-top container 3 to scrape off any sludge that may be adhering to sides of the open-top container 3. After the aforementioned operations are completed, the rod 1 and the filter mesh 2 are reset, and sealing elements 14 need to be installed on the two base plates 6 to ensure a sealing effect of the monitoring device.

Preferably, the rod 1 is equipped with scale lines, and the scale lines can control a depth of the wastewater collection.

Preferably, the marker ring 10 is sleeved to the rod 1.

In the description of the disclosure, it should be understood that terms such as "longitudinal", "lateral", "up", "down", "front", "back", "left", "right" "vertical", "horizontal", "top", "bottom", "inner" and "outer" which indicate directions or positional relationships are based on the directions or positions shown in the accompanying drawings. They are used solely for the purpose of describing the disclosure and do not imply that the devices or components referred to must have specific orientations or be constructed and operated in specific directions. Therefore, they should not be construed as limitations on the disclosure.

Apparently, the above embodiment of the disclosure is merely an example made to clearly illustrate the disclosure, and is not intended to limit the ways in which the disclosure can be implemented. For those skilled in the art, various other forms of modifications or changes can still be made on the basis of the above description. It is not necessary, nor is it possible, to exhaust all possible implementations here. Any modifications, equivalent substitutions, and improvements made within the spirit and principles of the disclosure should all be included within the scope of protection of the claims of the disclosure.

What is claimed is:

1. A monitoring method of dissolved greenhouse gases in wastewater, comprising the following steps:

S1, collecting a wastewater sample by using a wastewater collection device, performing mud-water separation on the wastewater sample, and collecting a supernatant after the mud-water separation by using a headspace vial;

S2, adding a dilute sulfuric acid solution to the supernatant collected in the headspace vial to adjust pH of the supernatant to 1-4, and then tightening a cap of the headspace vial;

S3, inverting the headspace vial, checking whether there are air bubbles in the headspace vial, discarding the wastewater sample and repeating the step S1 and the step S2 to recollect another wastewater sample when there are air bubbles in the headspace vial, and storing the headspace vial in a refrigerator when there are no air bubbles in the headspace vial;

S4, injecting 5-10 milliliters (mL) of pure nitrogen into the headspace vial by using a syringe, and discharging 5-10 mL of the wastewater sample from the headspace vial through a conduit;

S5, placing the headspace vial in a water bath constant temperature shaker, and shaking the headspace vial for 20-30 minutes to make a gas phase and a liquid phase in the headspace vial to reach headspace equilibrium;

S6, measuring a temperature of the headspace vial in the step 5, measuring volumes of the gas phase and the liquid phase in the headspace vial in the step 5, extracting gases from an upper part of the headspace vial in the step S5, and measuring concentrations of the gases by using a gas chromatograph; and S7, quantitatively calculating concentrations of the dissolved greenhouse gases in the wastewater sample of the step S1 based on Henry's Law and the concentrations of the gases as greenhouse gases in the gas phase measured in the step S6;

wherein the dissolved greenhouse gases comprise nitrous oxide ($N_2O$) and methane ($CH_4$);

wherein a concentration calculation equation for the $N_2O$ is:

$$C_0 = \frac{(C_l \times V_l) + \left(\frac{C_g \times P}{R \times T} \times V_g\right)}{V_l + V_g}$$

$$C_l = C_g \times \exp\left(\left(A_1 + A_2 \times \left(\frac{100}{T}\right) + A_3 \times \ln\left(\frac{T}{100}\right) + A_4 \times \left(\frac{T}{100}\right)^2\right)\right)$$

where $C_0$ represents a concentration of the $N_2O$ in the wastewater sample, $C_g$ represents a concentration of the $N_2O$ in the gas phase after the headspace equilibrium, $C_l$ represents a concentration of the $N_2O$ in the liquid phase after the headspace equilibrium, and P and R respectively represent an atmospheric pressure and a gas constant; T represents an absolute temperature, $V_g$ and $V_l$ respectively represent the volumes of the gas phase and the liquid phase in the headspace vial, and $A_1$, $A_2$, $A_3$ and $A_4$ respectively represent constants −165.8806, 222.8743, 92.0792, and −1.48425; and wherein a concentration calculation equation for the $CH_4$ is:

$$C_0 = C_g\left(\frac{\beta RT}{V_m} + \frac{V_g}{V_l}\right)$$

where $C_0$ represents a concentration of the $CH_4$ in the wastewater sample, $C_g$ represents a concentration of the $CH_4$ in the gas phase after the headspace equilibrium, β represents a solubility coefficient for the $CH_4$, R represents a gas state constant, T represents the absolute temperature, $V_m$ represents a molar volume of the $CH_4$ under a standard condition, and $V_g$ and $V_l$ respectively represent the volumes of the gas phase and the liquid phase in the headspace vial.

2. The monitoring method as claimed in claim 1, wherein a mass fraction of the dilute sulfuric acid solution in the step S2 is 20%.

3. The monitoring method as claimed in claim 1, wherein a storage temperature of the refrigerator in the step S3 is 0 degrees Celsius (° C.) to 4° C.

4. The monitoring method as claimed in claim 1, wherein the step S5 specifically comprises: placing the headspace vial in the water bath constant temperature shaker and shaking the headspace vial under a condition of 25° C. and 150-200 revolutions (r) per minute for 20-30 minutes.

5. A monitoring device of the dissolved greenhouse gases in the wastewater, based on the monitoring method as claimed in claim 1, comprising:
an open-top container (3), wherein two base plates (6) are capable of horizontally sliding and are symmetrically disposed on a bottom of the open-top container (3), sliding seats (7) are fixedly connected to top surfaces of the two base plates (6) respectively, the sliding seats (7) are disposed on ends of the two base plates (6) close to each other, and the sliding seats (7) are horizontally slide-connected to sliding rods (8) respectively; ends of the sliding rods (8) are fixedly connected to an inner wall of the open-top container (3) respectively, springs (9) are fixedly connected between the sliding seats (7) and the inner wall of the open-top container (3) respectively, and the springs (9) are respectively sleeved to the sliding rods (8);
a rod (1), vertically disposed in the open-top container (3); wherein a bottom of the rod (1) is hinged to two hinge rods (11), the two hinge rods (11) are respectively hinged to the sliding seats (7) disposed on the top surfaces of the two base plates (6), the rod (1) is slidably connected to a filter mesh (2) with position limiting, the filter mesh (2) is slidably matched to the inner wall of the open-top container (3), an outer wall of the rod (1) is threadedly connected to a threaded sleeve (12), and the threaded sleeve (12) is rotatably connected to a top end of the filter mesh (2); and
a connecting pipe (5), horizontally and fixedly connected to a side wall of the open-top container (3), wherein a valve (4) is disposed on the connecting pipe (5).

6. The monitoring device as claimed in claim 5, wherein the rod (1) is equipped with scale lines.

7. The monitoring device as claimed in claim 5, wherein a marker ring (10) is sleeved to the rod (1).

* * * * *